United States Patent
Di Stasi et al.

(10) Patent No.: US 10,292,584 B2
(45) Date of Patent: May 21, 2019

(54) SYSTEMS AND METHODS FOR USING EYE MOVEMENTS TO DETERMINE STATES

(71) Applicant: DIGNITY HEALTH, San Francisco, CA (US)

(72) Inventors: Leandro Luigi Di Stasi, Granada (ES); Susana Martinez-Conde, Brooklyn, NY (US); Raul Cabestrero, Madrid (ES); Andres Catena, Granada (ES); Michael McCamy, Phoenix, AZ (US); Stephen L. Macknik, Brooklyn, NY (US)

(73) Assignee: Dignity Health, San Francisco, CA (US)

( * ) Notice: Subject to any disclaimer, the term of this patent is extended or adjusted under 35 U.S.C. 154(b) by 0 days.

(21) Appl. No.: 15/115,370

(22) PCT Filed: Jan. 29, 2015

(86) PCT No.: PCT/US2015/013551
§ 371 (c)(1),
(2) Date: Jul. 29, 2016

(87) PCT Pub. No.: WO2015/116832
PCT Pub. Date: Aug. 6, 2015

(65) Prior Publication Data
US 2017/0000339 A1    Jan. 5, 2017

Related U.S. Application Data

(60) Provisional application No. 61/933,259, filed on Jan. 29, 2014.

(51) Int. Cl.
*A61B 3/113* (2006.01)
*A61B 5/11* (2006.01)
(Continued)

(52) U.S. Cl.
CPC .......... *A61B 3/113* (2013.01); *A61B 5/11* (2013.01); *A61B 5/1103* (2013.01);
(Continued)

(58) Field of Classification Search
CPC ....... A61B 3/113; A61B 3/0025; A61B 3/112; G06K 9/00604; G06K 9/00597
(Continued)

(56) References Cited

U.S. PATENT DOCUMENTS 7,795,218 B2 * 9/2010 McKerracher ......... A61K 47/60
514/17.7
2008/0188777 A1 * 8/2008 Bedziouk ................. A61B 5/16
600/595
(Continued)

FOREIGN PATENT DOCUMENTS

WO    2009/066109    5/2009
WO    2013/078461    5/2013

OTHER PUBLICATIONS

The International Search Report and Written Opinion as dated May 11, 2015 for International Application PCT/US2015/013551.
(Continued)

*Primary Examiner* — Mohammed A Hasan
(74) *Attorney, Agent, or Firm* — Quarles & Brady LLP

(57) ABSTRACT

Systems and methods for detecting onset, presence, and progression of particular states, including hypoxia, include observing eye movements of a subject to and correlating the observed movements to known baseline or hypoxic conditions. A detection system may record eye movement data from a user, compare the eye movement data to a data model comprising threshold eye movement data samples, and from the comparison make a determination whether or not hypoxia, fatigue, or other detrimental conditions are present. The detection system may alert the user to take corrective
(Continued)

action if onset or presence of a dangerous condition is detected. The eye movements detected include saccadic and intersaccadic parameters such as intersaccadic drift velocity. Measurements may be collected in situ while the subject is performing normal duties, processed to determine indicators of detrimental conditions, and reported to the subject within a few seconds.

20 Claims, 6 Drawing Sheets

(51) Int. Cl.
*A61B 5/145* (2006.01)
*A61B 5/00* (2006.01)

(52) U.S. Cl.
CPC ........ *A61B 5/14542* (2013.01); *A61B 5/4064* (2013.01); *A61B 5/7278* (2013.01)

(58) Field of Classification Search
USPC ................................ 351/205, 209, 210, 246
See application file for complete search history.

(56) References Cited

U.S. PATENT DOCUMENTS

2012/0238903 A1* 9/2012 Martinez-Conde .... A61B 3/113
    600/558
2017/0007119 A1* 1/2017 Cornsweet ............. A61B 3/113

OTHER PUBLICATIONS

Di Stasi et al., MicroSaccade and Drift Dynamics Reflect Mental Fatigue, European Journal of Neuroscience, 2013, p. 1-10. [Retrieved on Apr. 6, 2015]. Retrieved from the interet: <URL: http://www.neuralcorrelate.com/smc_lab/files/publications/distasi_etal_ejn13.pdf>.

* cited by examiner

SYSTEMS AND METHODS FOR USING EYE MOVEMENTS TO DETERMINE STATES

CROSS-REFERENCE TO RELATED APPLICATIONS

This application represents the national stage entry of PCT International Application No. PCT/US2015/013551 filed Jan. 29, 2015 and claims priority to U.S. Provisional Patent Application No. 61/933,259 filed Jan. 29, 2014. The contents of this application are hereby incorporated by reference as if set forth in their entirety herein.

STATEMENT REGARDING FEDERALLY SPONSORED RESEARCH

This invention was made with government support under Grant PS-2010-0667 by the Spanish Ministry of Education. The government of Spain has certain rights in the invention.

BACKGROUND

The present disclosure generally relates to systems and methods for acquiring data from a subject and, more particularly, to systems and methods for gathering and analyzing information about the subject's eye movements to determine or predict a state of the subject, including conditions such as hypoxia.

Human brain function is highly vulnerable to hypoxic insults. Hypoxia impairs vision, cognition, motor control, and can cause severe incapacitation and death. Reports on the effects of hypoxia on visual function (i.e. dark adaptation, central brightness contrast, color vision, and central acuity) have been confounded by subjective and environmental factors (i.e. changes in ambient light level and non-compliance by flight crews in accurately reporting physiological disabilities such as color blindness). The few studies that have addressed the effects of hypoxia on objective oculomotor metrics, such as saccadic velocity, have obtained inconsistent results. The question of whether hypoxia modulates oculomotor metrics therefore remains open.

Acute hypoxia, defined as decreased availability of oxygen in the body's tissues that can lead to dyspnea, rapid pulse, syncope, visual dysfunction, and mental disturbances such as delirium or euphoria, is one of the most serious single hazards in military and civil aviation. Thus, international organizations such as the US Federal Aviation Administration and the European Aviation Safety Agency recommend hypoxia training (i.e. performance training while reducing oxygen availability to the trainee) as a mandatory part of flight and cabin crew instruction. Altitude chamber training—a well-established method to train aircrews to recognize early symptoms and signs of hypoxia—has not eliminated in-flight hypoxic incidents, however. A complicating factor is that there are wide individual differences in tolerance to acute and chronic exposures to reduced oxygen environments.

Early and objective detection of the physiological effects of hypoxia can preempt these symptoms, and is critical to prevent catastrophes in civil and military aviation. Considering the above, there continues to be a clear need for rapid, accurate, and non-invasive individualized systems and methods for detecting the presence or onset of hypoxia.

BRIEF SUMMARY

The present invention overcomes drawbacks of previous technologies by providing systems and methods that afford a number of advantages and capabilities not contemplated by, recognized in, or possible in traditional system or known methodologies related to tracking or determining a subject's state, including the detection of hypoxia.

In one embodiment, the present disclosure provides a system including a sensing arrangement that collects eye movement data of a user, an alerting arrangement that produces an alert to the user in response to receipt of an alert signal, and a control unit in communication with the sensing arrangement and the alerting arrangement. The control unit includes a data analysis module configured to extract one or more current eye movement dynamics from the eye movement data, and a comparison module configured to receive the one or more current eye movement dynamics from the data analysis module and compare the one or more current eye movement dynamics to one or more baseline eye movement dynamics accessible by the control unit, and to send the alert signal to the alerting arrangement in response to a determination that one or more of the compared current eye movement dynamics diverges from one or more of the baseline eye movement dynamics by a threshold amount.

The current eye movement dynamics may include one or more intersaccadic drift velocities of the user and the data analysis module is configured to calculate the one or more intersaccadic drift velocities. The comparison module may be configured to compare one or more of the intersaccadic drift velocities to one or more threshold drift velocities of the baseline eye movement dynamics. One of the intersaccadic drift velocities may be a drift mean velocity. When the drift mean velocity is different from the one or more threshold drift velocities by more than the threshold amount, the alert signal may be an alert of the presence of hypoxia in the user. One of the intersaccadic drift velocities may be a current intersaccadic drift velocity. When the current intersaccadic drift velocity is different from the one or more threshold drift velocities by more than the threshold amount, the alert signal may be an alert of the onset of hypoxia in the user. The current intersaccadic drift velocity may be collected by the sensing arrangement within ten seconds of the comparison module sending the alert signal to the alerting arrangement. The data analysis module may calculate the current intersaccadic drift velocity by identifying, in the eye movement data, a drift period comprising a duration and a distance and determining the intersaccadic drift velocity from the duration and the distance.

The eye movement dynamics may include one or more saccade parameters. The saccade parameters may include a saccadic peak velocity and a magnitude. The comparison module may be configured to compare the current intersaccadic drift velocity to one or more threshold drift velocities of the baseline eye movement dynamics.

The eye movement data may be collected from both eyes of the user. The baseline eye movement dynamics may be obtained from a data model stored in a model data store accessible by the control unit. The data model may be a standardized model generated from baseline measurements of one or more non-user subjects. The control unit may configured to calibrate the data model to the user by obtaining, from the sensing arrangement when the user is in a non-hypoxic state, a calibration set of eye movement data, comparing the calibration set to the standardized model to determine a deviation of the calibration set from the standardized model, and adapting the data model to the user based on the deviation. The calibration set may include a threshold-normal drift velocity for the user, and comparing the calibration set to the standardized model may include comparing the threshold-normal drift velocity for the user to a threshold-normal drift velocity for the standardized model. The control unit may further include a data model generator configured to generate the data model by obtaining, from the sensing arrangement when the user is in a non-hypoxic state, a portion of the eye movement data, extracting from the portion of the eye movement data a plurality of threshold eye movement data samples, and creating the data model from the threshold eye movement data samples.

In another embodiment, the present disclosure provides a method of determining a physiological state of a user. The method includes recording from the user, during a time-on-duty of the user, eye movement data of one or both of the user's eyes without interrupting an activity of the user, comparing the eye movement data to one or more baseline measurements, and, if the eye movement data diverges from one or more of the baseline measurements by a threshold amount, delivering an alert to the user. The eye movement data may include one or both of saccade parameters and intersaccadic drift parameters. The method may further include calculating a current intersaccadic drift velocity of the user from the eye movement data. Comparing the eye movement data to the baseline measurements may include comparing the current intersaccadic drift velocity to a threshold intersaccadic drift velocity of the baseline measurements. The alert may indicate to the user that a hypoxic condition of the user exists.

The method may further include recording the baseline measurements from the user in non-hypoxic conditions. The method may further include obtaining a standardized data model of eye movement dynamics, recording one or more threshold eye movement data samples from the user in non-hypoxic conditions, determining a deviation of the threshold eye movement data samples from one or more eye movement dynamics of the standardized model, and using the deviation to calibrate the standardized data model to include the baseline dynamics.

In one embodiment of the present invention, systems and methods are provided for monitoring, recording, and/or analyzing eye movements in situ to determine whether oculomotor dynamics are being affected by the onset or presence of hypoxia. In one aspect, a sensor arrangement may include a camera and recording assembly for detecting and recording the eye movements.

In some contemplated embodiments, systems and methods using in situ testing of eye movement dynamics may be employed to identify the onset or presence of states or physiological conditions, such as fatigue, hypoxia, stroke, intoxication, seizure, and other conditions. The described study has shown that eye saccades and the velocity of intersaccadic eye drift are detectably affected by the onset or presence of these conditions. A system and method that implements the data recording and analysis approaches of the study may alert a user to the presence of these states or conditions in a testing environment. In particular, a system in accordance with the present invention may include devices and device assemblies that record baseline data of a subject and generate a data model representing the eye movement data of the subject, and further the system may include device and device assemblies that record eye movement data in situ and compare it to the data model to determine if the user is experiencing or about to experience any of the dangerous conditions.

In a contemplated embodiment of the present invention, a system includes a sensing arrangement that collects eye movement data of a user, and a control unit in communication with the sensing arrangement. The control unit may be configured to compare the eye movement data to one or more baseline measurements of eye movement dynamics and, if the eye movement data diverges from one or more of the baseline measurements by a threshold amount, generate an alert for delivery to the user. Comparing the eye movement data to the baseline measurements may include calculating a current intersaccadic drift velocity of the user and comparing the current intersaccadic drift velocity to one or more threshold drift velocities of the baseline measurements. The eye movement data may include one or more saccade parameters, and comparing the eye movement data to the baseline measurements may include calculating a current intersaccadic drift velocity of the user from the saccade parameters and comparing the current intersaccadic drift velocity to one or more threshold drift velocities of the baseline measurements.

In another embodiment of the present invention, a method of determining a physiological state of a user includes recording from the user eye movement data of one or both of the user's eyes, comparing the eye movement data to one or more baseline measurements, and, if the eye movement data diverges from one or more of the baseline measurements by a threshold amount, delivering an alert to the user. The eye movement data may include one or both of saccade parameters and intersaccadic drift parameters.

In another embodiment of the present invention, systems and methods of the present invention may be combined as a kit or apparatus, whose advantages and capabilities will be readily apparent from descriptions below.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The present invention will hereafter be described with reference to the accompanying drawings, wherein like reference numerals denote like elements.

DETAILED DESCRIPTION

Systems and methods for detecting onset, presence, and progression of particular states, including hypoxia, through observation of eye movements are described herein. These systems and methods can be further understood through the results of one or more experiments by the inventors. The results show that acute hypoxia affects oculomotor dynamics, including saccadic metrics and intersaccadic drift metrics, with increasing severity as the hypoxia progresses. The results show, in particular, that intersaccadic drift velocity increases as acute hypoxia develops and progresses, and that select oculomotor dynamics can be tracked against a baseline to alert a subject before the effects of hypoxia impair the subject's ability to take corrective action. What follows are descriptions of a particular study and its results, and methods for practical application of the findings in a detection system.

Study and Results

The systems and methods may be understood by way of example data obtained through experimentation. The example data are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims. For example, specific duty conditions and pre-experimental training of participants are provided, although it will be appreciated that the systems and methods may be applied in any oxygen-depleted environment and for any subject without undue experimentation.

Materials and Methods

The study was conducted in conformity with the declaration of Helsinki and the Spanish Defence Medical Inspector General's Office's IRB (approval date: Jul. 26, 2012). Written informed consent was obtained from each participant. Participants attended the Spanish Defence Aero-medical Center (CIMA) for aviation medicine training. Most subjects were members of the Spanish Air Force flight crew (i.e., pilots and flight engineers). All subjects had normal or corrected-to-normal vision and underwent a full physical examination prior to study participation. Six male subjects, most of them aircrew operating rotary wing aircrafts receiving hypoxia training (mean age, height, and weight: 37 yrs (±6.4); 176 cm (±5.1); 85 kg (±8.5)), comprised the hypoxia group. Six different male subjects, receiving no hypoxia training (mean age, height, and weight: 35 yrs (±11); 181 cm (±3.8); 83 kg (±7.3)), comprised the control group.

The study followed a Pre/Post-Test design. The hypoxia training was the between-subjects factor and the eye movement metrics, including intersaccadic drift (hereafter drift) velocity, and saccadic velocity and magnitude, were the dependent variables. We also recorded the participants' subjective level of fatigue via standardized questionnaires.

Figure 1A:
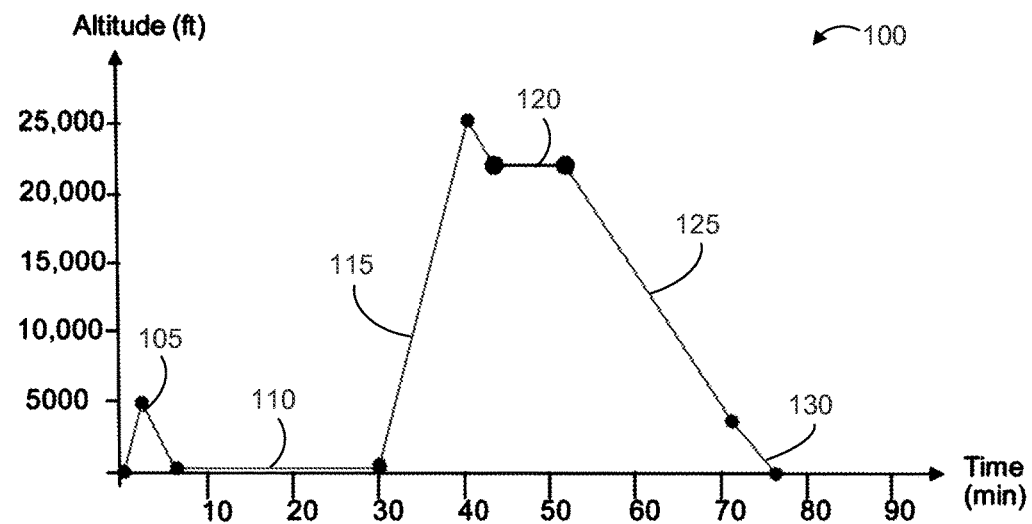
FIGS. 1A-B are charts illustrating an oculomotor performance experiment in accordance with the present invention.
Figure 1B:
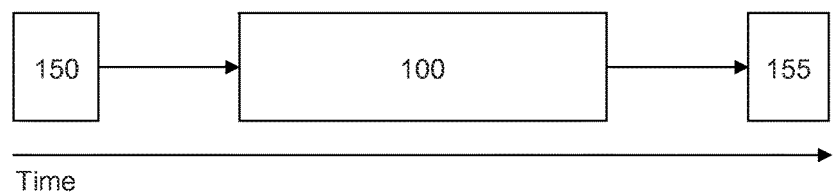

The CIMA altitude training chamber, manufactured by Environmental Tectonics Corporation, USA, is a computer-controlled, man-rated, low-pressure chamber that accommodates 10 subjects and one inside safety observer. A vacuum pump removes pressure from the chamber to simulate the pressure of a particular altitude. The CIMA training involves various hypobaric training regimes; in this study we used training Type 1b, which consists of depressurizing the hypobaric chamber to a simulated maximum altitude of 25,000 ft, to conduct a demonstration of acute hypoxia. FIGS. 1A and 1B illustrate the details of this design. FIG. 1A is a chart of a simulated flight 100 showing altitude as a function of time, and FIG. 1B illustrates the associated timeline of administering the saccade tasks.

Referring to FIG. 1A, an initial ear and sinus check ascent to 5,000 ft MSL, at stage 105, is followed by a 30-minute denitrogenation period at ground level, with the subjects breathing 100% oxygen via a pressure-demand-type oxygen mask, at stage 110. At stage 115, subjects experience an ascent to 25,000 ft, and at stage 120 hypoxia conditions are administered at a rate of about 10 mins total, with each subject undergoing hypoxia for up to 3.25 min without supplemental oxygen. At stages 125 and 130, the subjects undergo a simulated descent to ground level. The total duration of the simulated flight was about 73 mins. Referring to FIG. 1B, the experiment began by administering a Pre-Test guided saccade task 150, followed be administering the simulated flight 100, and finished with administration of a Post-Test guided saccade task 155 that was the same task as the Pre-Test guided saccade task 150. Control subjects carried out their regular duties between the Pre- and Post-sessions. All participants filled in a self-rating scale of perceived fatigue before each oculomotor test.

As stated above, each subject experienced hypoxia (equivalent to an altitude of 22,000 ft) for a maximum of 3.25 min without supplemental oxygen. All subjects exhibited cognitive impairment during the hypoxia exposure, as indicated by the standard hypoxia demonstration sheet (i.e., pencil and paper test) known in the art. Pulse oximetry, measured with a non-invasive pulse oximeter on the subject's non-writing-hand's fingertip, confirmed a final oxy-hemoglobin saturation between 62-77% (±5.9) $S_pO_2$ in each subject.

Before and after the subjects entered the hypoxic chamber, we assessed their oculomotor dynamics via the guided saccade task 150,155, in which we displayed visual stimuli on a 21-in CRT screen (864×1152 pixels, refresh rate 100 Hz) located ~70 cm in front of the subject, who sat on a comfortable chair. This task induced a total of 336 saccades, including vertical, diagonal, and horizontal directions. Subjects completed the task in ~15 minutes. Eye position was sampled binocularly at 500 Hz using the desktop configuration of the EyeLink 1000 eye tracking system manufactured by SR Research, Ontario, Canada. Data recordation included detecting and classifying eye movements and calculating a linear regression on the log-transformed saccadic peak velocities as a function of their magnitudes for each subject, where the slope reflected the effect of hypoxia on the saccadic peak velocity-magnitude relationship.

The more specific methods of recording and analyzing eye movements are as follows. Eye movements were sampled binocularly at 500 Hz using the desktop configuration of the Eyelink 1000 eye tracking system with a resolution of 0.01° RMS. Blink periods were identified as portions of the raw data where pupil information was missing, and were removed. Additionally, portions of data where very fast decreases and increases in pupil area occurred (>50 units/sample) were classified as semi-blinks where the pupil is never fully occluded, and were removed. 200 ms were added before and after each blink/semi-blink to eliminate the initial and final parts where the pupil was still partially occluded. Saccades were identified with a modified version of the algorithm developed by Engbert and Kliegl (Engbert & Kliegl, 2003; Engbert, 2006; Engbert & Mergenthaler, 2006) with λ=6 (used to determine the velocity threshold for saccade detection) and a minimum saccadic duration of 6 ms. To reduce the amount of potential noise, only binocular saccades (i.e., saccades with a minimum overlap of one data sample in both eyes) were considered. Additionally, a minimum intersaccadic interval of 20 ms was imposed, so that potential overshoot corrections might not be categorized as new saccades. To calculate saccade properties such as magnitude and peak velocity, the values for the right and left eyes were averaged. Table 2 includes the descriptive statistics for saccades and drift.

Drift periods were defined as the eye-position epochs between saccades, overshoots, and blinks. 10 ms were removed from the start and end of each drift period (because of imperfect detection of blinks and small saccades), and the remaining eye-position data was filtered with a low-pass Butterworth filter of order 13 and a cut-off frequency of 30 Hz. To calculate drift parameters (such as mean velocity and duration), an additional 10 ms was removed from the beginning and end of each drift period of the filtered data, to reduce edge effects due to the filter. Drifts shorter than 200 ms were discarded. Finally, because drifts are not generally conjugate, data from both the left and right eye was used. Thus, any given drift period had a duration, distance (length of the curve traced out by the drift), peak velocity, and mean velocity for each eye.

Subjective fatigue is a well-known effect of both hypoxia and time on-duty (TOD). Thus, the effects from hypoxia on oculomotor metrics were disambiguated from those of TOD by requiring participants to complete a self-rating scale of perceived fatigue, as is known in the art, before each oculomotor test.

All subjects received a standard briefing on the effects of simulated altitude and hypoxia on the day preceding the experiment. On the day of the training, aircrews underwent hypoxia training and two measuring sessions (see FIG. 1B) between 9.00 am and 12.30 pm (approximately three hours elapsed between the two sessions). The interval between the return to sea level and the start of the Post-Test session was ~30 minutes. Control subjects carried out their regular duties between the Pre- and Post-sessions.

The oculomotor parameters were analyzed following two separate (one for each dependent variable) 2×2 repeated-measures analyses of covariance (ANCOVAs). Subjective scores of perceived fatigue served as covariates, and measuring session and group served as factors. This analysis provided statistical control for the influence of TOD on the eye movement variables. For the subjective scores of perceived fatigue, a 2×2 repeated-measures analysis of variance (ANOVA) was used, with the two measuring sessions (Pre-Test vs. Post-Test) as the within-subjects factor and the group (experimental vs. control group) as the between-subjects factor.

Results

Table 1 includes aggregate collected data for the subjective, saccadic, and intersaccadic drift parameters. The scores of the self-rating scale of perceived fatigue (Borg's Scale) range between 6 and 20. Higher scores indicate more subjective fatigue. The eye movement data includes the calculated means and standard deviations (in parentheses) from the mean values of each subject in each group (n=6). The adjusted means (in square brackets) refer to the group means after controlling for the effect of TOD (i.e. by considering the scores of the self-rating scale of perceived fatigue as covariates (ANCOVA adjusted means)).

TABLE 1

| | Pre-Test | | Post-Test | |
| --- | --- | --- | --- | --- |
| | Control Group | Experimental Group | Control Group | Experimental Group |
| Drift Mean Velocity (deg/sec) | 2.31 [2.25] (0.35) | 2.30 [2.35] (0.75) | 2.50 [2.34] (0.44) | 2.85 [2.99] (1.09) |
| Slope | 0.69 | 0.68 | 0.69 | 0.67 |

TABLE 1-continued

| | Pre-Test | | Post-Test | |
| --- | --- | --- | --- | --- |
| | Control Group | Experimental Group | Control Group | Experimental Group |
| Saccadic Magnitude/ Peak Velocity (deg/sec) | [0.69] (0.04) | [0.68] (0.04) | [0.69] (0.04) | [0.67] (0.05) |
| Borg Scale | 6.67 (2.9) | 7.67 (2.0) | 8.67 (2.1) | 8.67 (2.7) |

Table 2 is a more detailed summary of the collected data for intersaccadic drift parameters and saccadic parameters. Means and standard deviations were calculated from the mean values of each subject for each group (n=6). "*" denotes statistical significance for the "Group×Measuring Time" interaction. The adjusted means (in square brackets) refer to the group means after controlling for the effect of TOD by considering the scores of the self-rating scale of perceived fatigue as covariates (ANCOVA adjusted means). All p-values <0.05.

TABLE 2

| | Experimental Group | | Control Group | |
| --- | --- | --- | --- | --- |
| | Pre-Test | Post-Test | Pre-Test | Post-Test |
| INTERSACCADIC DRIFT PARAMETERS | | | | |
| Mean Velocity (deg/sec) | 2.29 [2.35] (0.76) | 2.85 [2.99] (1.10) | 2.31 [2.25] (0.35) | 2.48 [2.34] (0.44) |
| Peak Velocity (deg/sec) | 6.26 [6.50] (2.08) | 7.88 [8.21] (2.21) | 7.26 [7.04] (2.51) | 7.00 [6.67] (1.59) |
| Distance (deg) | 0.90 [0.92] (0.27) | 1.06 [1.10] (0.36) | 1.05 [1.02] (0.18) | 1.00 [0.95] (0.15) |
| Duration (ms) | 0.42 [0.42] (0.07) | 0.39 [0.39] (0.06) | 0.47 [0.47] (0.04) | 0.44 [0.44] (0.05) |
| Number | 2205 [2180] (187) | 2164 [2133] (194) | 2091 [2117] (187) | 2132 [2136] (194) |
| SACCADES PARAMETERS | | | | |
| Slope (peak velocity/ magnitude) | 0.69 [0.69] (0.04) | 0.68 [0.68] (0.04) | 0.69 [0.69] (0.04) | 0.67 [0.67] (0.05) |
| Slope (mean velocity/ magnitude) | 0.56 [0.56] (0.02) | 0.55 [0.54] (0.02) | 0.54 [0.54] (0.04) | 0.52 [0.52] (0.04) |
| Slope (duration/ magnitude) | 0.46 [0.46] (0.02) | 0.48 [0.49] (0.03) | 0.48 [0.48] (0.05) | 0.50 [0.50] (0.05) |
| Mean Velocity (deg/sec) | 104.70 [105.69] (11.23) | 99.32 [99.60] (11.03) | 109.44 [108.46] (15.35) | 100.93 [100.65] (16.08) |
| Peak Velocity (deg/sec) | 219.97 [222.48] (36.69) | 198.29 [198.81] (30.13) | 237.12 [234.61] (37.74) | 208.86 [208.33] (42.61) |
| Magnitude (deg) | 4.73 [4.77] (0.75) | 4.29 [4.29] (0.88) | 5.42 [5.38] (0.65) | 4.94 [4.94] (0.93) |
| Duration (ms) | 35.54 [35.78] (4.06) | 33.28 [33.56] (3.17) | 41.66 [41.41] (5.74) | 38.50 [38.21] (5.45) |
| Rate [N/s] | 1.67 [1.68] (0.39) | 1.61 [1.64] (0.53) | 1.50 [1.48] (0.18) | 1.43 [1.40] (0.26) |

Figure 2A:
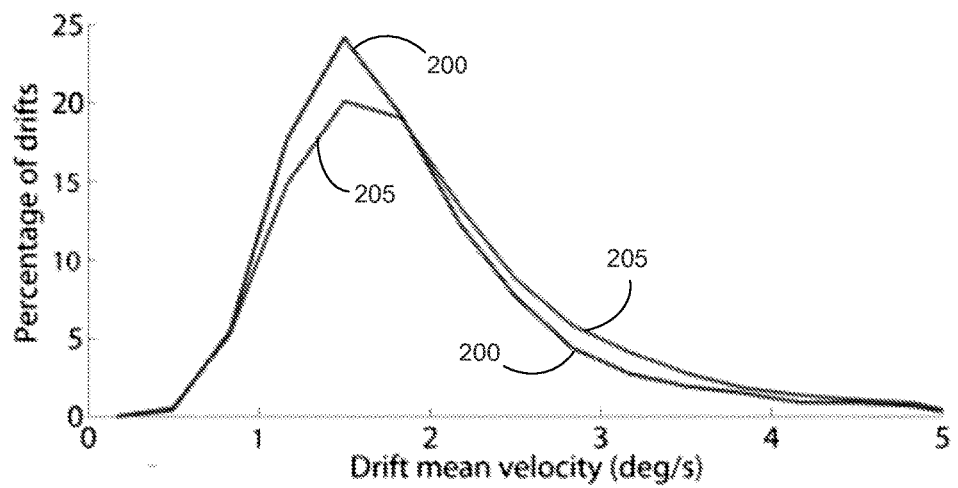
FIGS. 2A-B are charts illustrating experimental results regarding the intersaccadic drift mean velocity of experiment subjects in a hypoxia group (FIG. 2A) and in a control group (FIG. 2B).
Figure 2B:
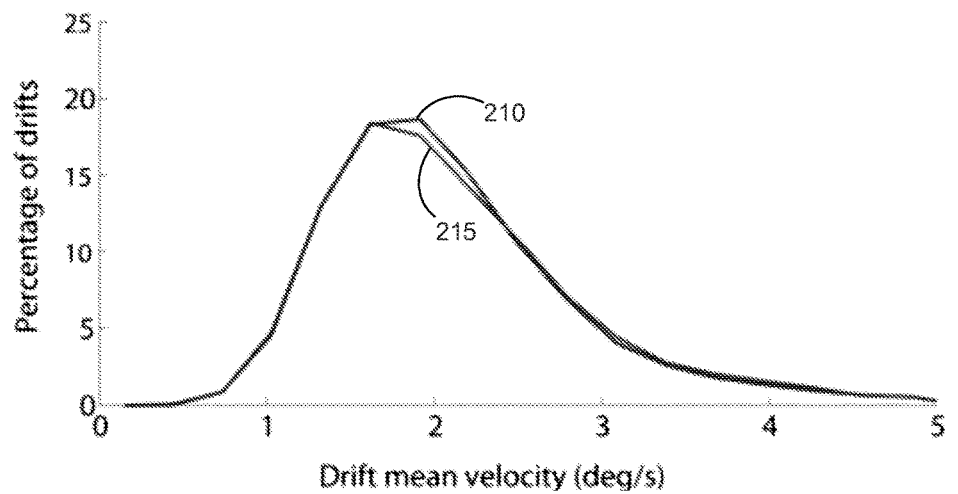

Referring to FIGS. 2A-B, there is illustrated the drift mean velocity distributions before and after hypoxia training for the hypoxia group (FIG. 2A) or equivalent TOD for the control group (FIG. 2B). Pre-Test is indicated by reference numerals 200 (FIG. 2A) and 210 (FIG. 2B), and Post-Test by reference numerals 205 (FIG. 2A) and 215 (FIG. 2B) for the subjects. In the hypoxia group, the average drift mean velocity increased from 2.35 deg/s to 2.99 deg/s after accounting for TOD, an increase of about 27%. In contrast, the control group average drift mean velocity changed by just 4% (from 2.25 to 2.34 deg/s), which is within the margin of error.

Figure 2C:
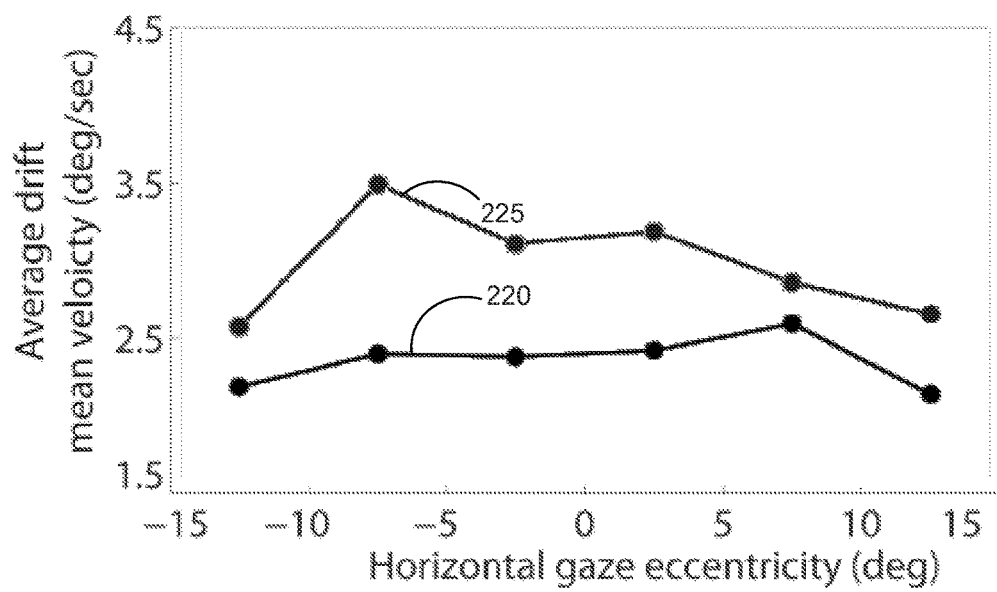
FIGS. 2C-D are charts illustrating experimental results regarding the average drift mean velocity of experiment subjects in a hypoxia group (FIG. 2C) and in a control group (FIG. 2D).
Figure 2D:
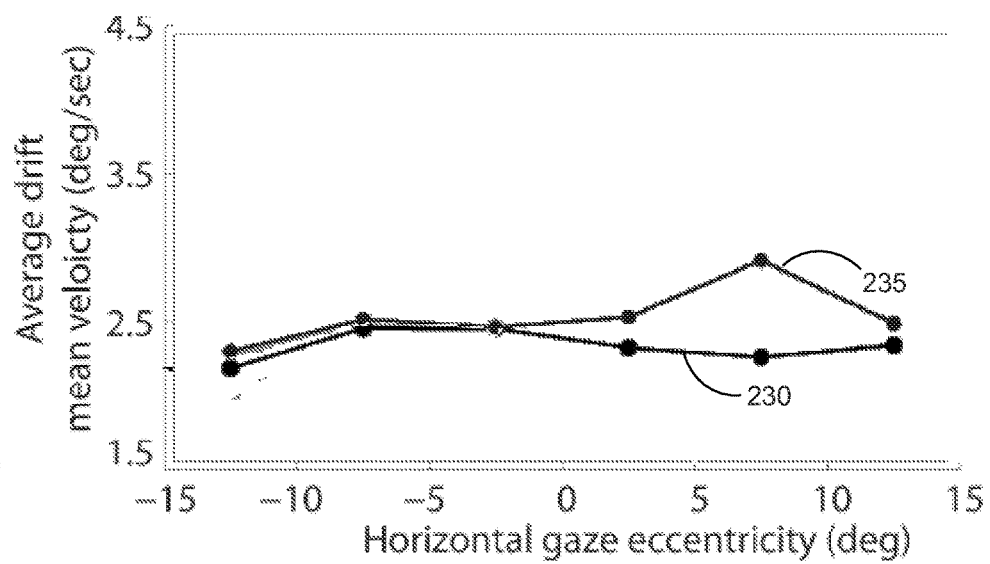

Referring to FIGS. 2C-D, there is illustrated the average drift mean velocity in degrees per second as a function of degrees of horizontal gaze eccentricity, before and after hypoxia training for the hypoxia group (FIG. 2C) or equivalent TOD for the control group (FIG. 2D). Pre-Test is indicated by reference numerals 220 (FIG. 2C) and 230 (FIG. 2D), and Post-Test by reference numerals 225 (FIG. 2C) and 235 (FIG. 2D) for the subjects. Mean drift velocity increased significantly from the Pre-Test to the Post-Test session in the hypoxia group, but not in the control group.

Figure 3A:
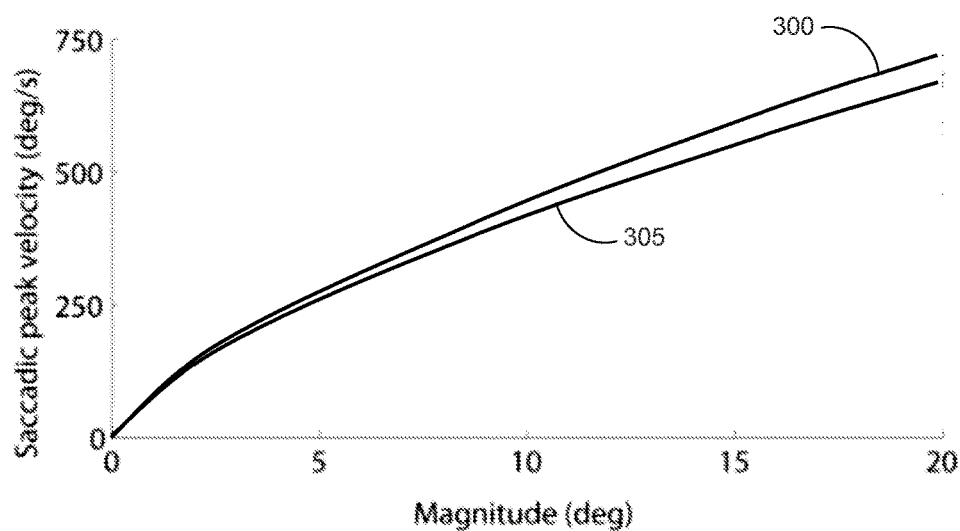
FIGS. 3A-B are charts illustrating experimental results regarding the saccadic peak velocity of experiment subjects in the hypoxia group (FIG. 3A) and in the control group (FIG. 3B).
Figure 3B:
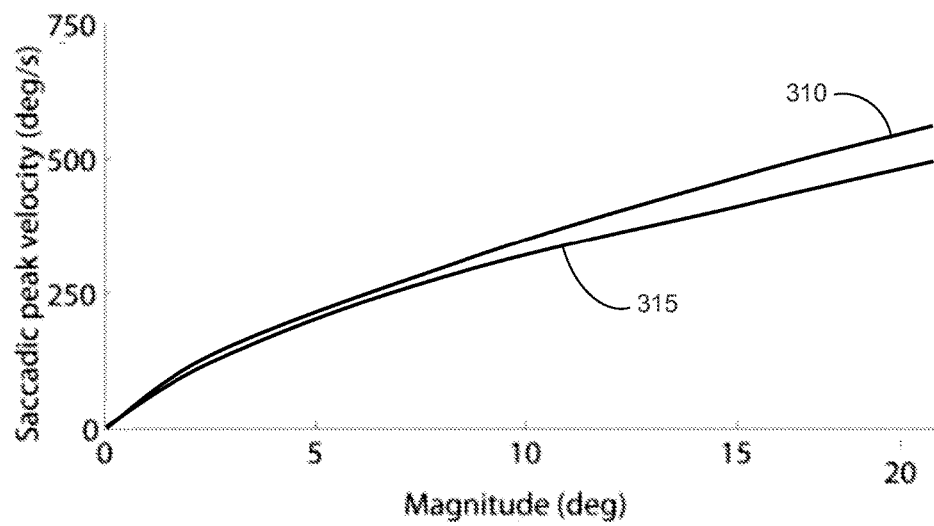

The results show that hypoxia induced an increase in the mean velocity of intersaccadic drift, suggesting a decrease in visual fixation stability. That is, drift mean velocity was significantly higher in the Post-Test session than in the Pre-Test session for the hypoxia group, but not for the control group, after controlling for the effect of TOD (i.e., by considering the scores of the self-rating scale of perceived fatigue as covariates [interaction between measuring session and group: $F(1,8)=10.192$, $p<0.013$; $\eta_p^2=0.56$]. Drift peak velocity and distance covered by drift were also significantly higher in the Post-Test than in the Pre-Test session for the hypoxia group, but not for the control group, consistent with the hypothesis of higher fixation instability with hypoxia (see Table 2). Drift duration was not affected (see Table 2). There were no significant main effect of hypoxia versus control groups or of Pre-versus Post-Test sessions [all F-values<3]. Saccadic peak velocity decreased from the Pre-Test to the Post-Test session for both hypoxia and control groups [$F(1,10)=7.32$, $p=0.02$] but the effect was not statistically significant when controlled for the influence of TOD. The average slope of saccadic peak velocity to saccadic magnitude between hypoxia and control groups was not statistically significant. FIGS. 3A-B illustrated the saccadic magnitude/peak velocity relationships for one experimental subject (FIG. 3A) and one control subject (FIG. 3B) at two different measuring times: Pre-Test (reference numerals 300 and 310) and Post-Test (reference numerals 305 and 315. The curves are the power-law fits to the data from each measuring session.

The results show that the slope of the saccadic magnitude/peak velocity relationship decreased from the Pre-Test to the Post-Test session in both the hypoxia and the control groups, suggesting that this effect was due to TOD rather than hypoxia. Indeed, when compensated for the influence of TOD (i.e., by considering the scores of the self-rating scale of perceived fatigue as covariates), no significant effects [all F-values<1] on the saccadic magnitude/peak velocity were found for either group. Saccadic magnitude/duration and saccadic magnitude/mean velocity relationships showed equivalent behaviors to the saccadic magnitude/peak velocity relationship (see Table 2). This is consistent with previous reports of the modulatory effects of TOD on saccade dynamics. Table 2 includes additional details about the effects of measuring session and group on other saccadic parameters.

As regards the self-rating scale of perceived fatigue, the degree of perceived fatigue increased from the Pre-Test to the Post-Test session in both groups [$F(1,10)=5$ $p=0.049$; $\eta_p^2=0.34$]. That is, increased TOD resulted in increased perceived fatigue in both groups. Neither the main effect of the group nor its interaction with the measuring sessions were significant [all F-values<1]. See Table 1.

Discussion

The results show that short-term hypobaric hypoxia gives rise to variations in drift velocity. Hypoxia-triggered increases in drift speed may indicate a decrease in fixation stability, and the rapid compensations of the oculomotor system to correct the ensuing fixation errors. This hypothesis is consistent with the observation that fixation instability is one of most frequent symptoms in patients suffering from cerebral visual-impairment (CVI) after a perinatal hypoxia-ischemia episode. CVI patients also exhibit abnormal smooth pursuit behavior. Drift is thought to be under the control of smooth eye movements. Thus, our present observations of increased drift speed after short-term hypoxia, combined with previous reports of impaired fixation instability and smooth pursuit in CVI patients, may indicate a common neural pathway by which decreased levels of oxygen in the brain lead to transitory or permanent oculomotor pathologies, depending on the duration of the hypoxia episode.

The effect of hypoxia on saccadic velocity in our study was no longer significant after controlling for the influence of fatigue due to TOD. Therefore, the decrease in saccadic peak velocities observed here is most parsimoniously explained by TOD, rather than hypoxia. Thus, the current study reconciles disparate results from previous studies.

One may wonder if the present changes in drift velocity might have resulted from increased head motion in the post-acute-hypoxia state. This possibility seems unlikely in light of previous research by some of the present co-inventors showing that the same eye-tracking system (Eye-Link 1000, SR Research) and forehead/chin rest used here could detect variations in drift velocity independently of head motion. Thus, the most parsimonious explanation for the current results is that drift velocity is indeed sensitive to hypobaric hypoxia.

In summary, short-term hypobaric hypoxia affected drift, but not saccade, velocities. This dissociation may arise at the level of the frontal pursuit area (FPA) in the cerebral cortex, an area dedicated to the control of slow eye movements, where the first sensory-to-motor transformation of low velocity eye movement signals takes place. FPA appears to provide commands that drive smooth eye velocity, and play an important role in modulating the setting of gain control. Short-term hypobaric hypoxia episodes may interfere with these commands, increasing eye instability as a result.

System and Methods for Detecting Dangerous Physiological Conditions, Including Hypoxia Using the approach of the present invention, a detection system may record eye movement data from a user, compare the eye movement data to a data model comprising threshold eye movement data samples, and from the comparison make a determination whether or not the user's brain function is suffering or is subject to hypoxic insult or other dangerous physiological conditions, such as fatigue. The detection system may alert the user to take corrective action if onset or presence of a dangerous condition is detected.

Figure 4:
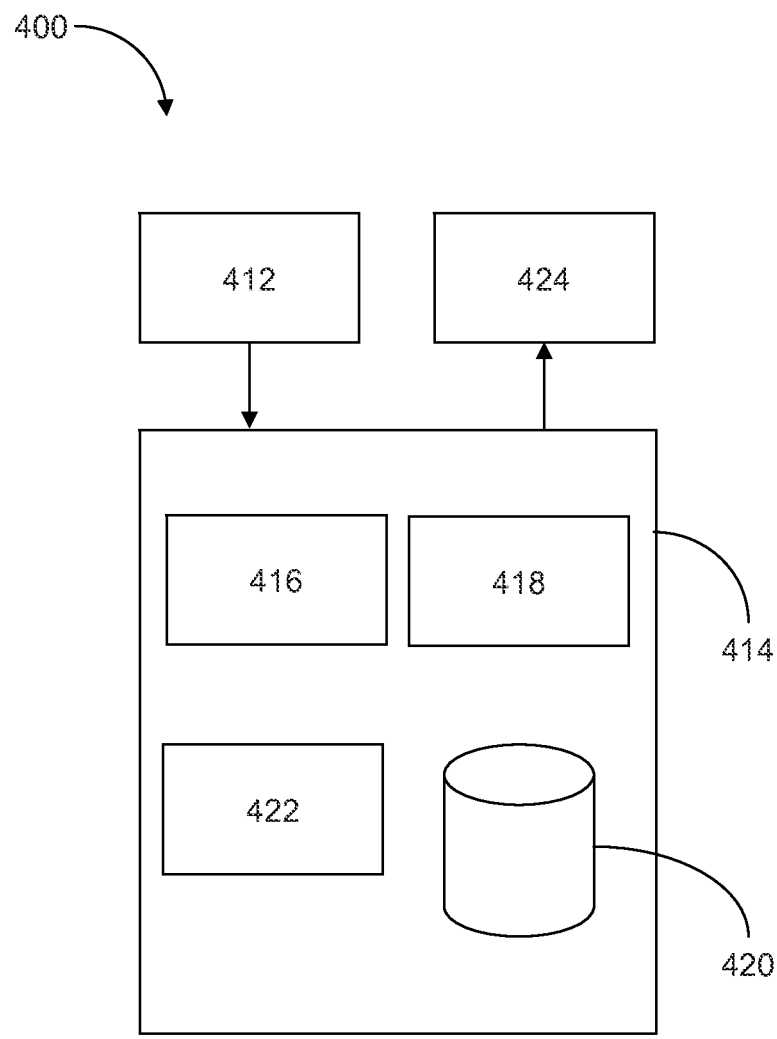
FIG. 4 is a diagram of a detection system in accordance with the present invention.

Referring to FIG. 4, an embodiment of a detection system 400 may include a sensing arrangement 412 configured to detect and record eye movement dynamics of the user. The sensing arrangement 412 may include one or more sensors suitable for collecting the eye movement data. Such sensors may include a camera or other imaging or motion tracking device capable of recording at a suitably high speed and level of detail so that the user's eye movement dynamics, including saccades and intersaccadic drift, are captured. A monocular arrangement of one or more sensors for one of the user's eyes may be used, or one or more sensors may be included for each eye to obtain binocular data. In some embodiments, the sensors may be miniaturized or otherwise compact, portable, and non-invasive so as not to interrupt an activity of the user while obtaining in situ measurements. The sensors may further be vehicle-independent, and may be wireless, to facilitate integration of the sensors into any deployment of the detection system 400. For example, the sensing arrangement 412 may include sensors that are integrated into eyewear, such as on the frame or within the lenses of a pair of glasses. This allows for eye movement data collected even as the user turns his head, and allows the sensors to be positioned close to the eyes. In another example, the sensors may be integrated into a heads-up display for a vehicle.

The sensing arrangement 412 may further include integrated or discrete devices for processing, storing, and transmitting collected data. Such devices may include a processor, volatile and/or permanent memory, a wired or wireless transmitter, and associated power circuits and power supply for operating the devices. Software modules may define and execute instructions for operating the sensors, configuring databases, registers, or other data stores, and controlling transmission of the data. The collected data may be shared via transmission to a control unit 414 that may be integrated with or disposed physically remotely from the sensing arrangement 412. The eye movement data, or a subset thereof, may be transmitted in real-time as it is captured by the sensors, or it may be stored for later transmission.

The control unit 414 may use the processing hardware (i.e., processor, memory, and the like) of the sensing arrangement 412, or may include its own processing hardware for analyzing the eye movement data and generating an alert to the user if needed. The control unit 414 may include a plurality of modules that cooperate to process the eye movement data in a particular fashion, such as according to the methods described below. Each module may include software (or firmware) that, when executed, configures the control unit 414 to perform a desired function. A data analysis module 416 may extract information from the eye movement data for comparison to the data model. The data analysis module 416 may include one or more data filters, such as a Butterworth or other suitable bandpass filter, that retain only desired signal elements of the eye movement data. The data analysis module 416 may include program instructions for calculating, from the eye movement data, one or more eye movement dynamics, such as saccades and/or intersaccadic drift velocities, of the user's eyes. The calculation may be performed substantially in real-time, such that a calculated intersaccadic drift velocity may be considered the current drift velocity of the user's eyes.

A comparison module 418 may receive the processed eye movement data from the data analysis module 416 and may compare it to the data model as described in detail below. The control unit 414 may include or have access to a model data store 420 that stores the data model. The model data store 420 may be a database, data record, register, or other suitable arrangement for storing data. In some embodiments, the data model may simply be a threshold drift velocity, and may thus be stored as a single data record in memory accessible by the comparison module 418. In other embodiments, the data model may be a lookup table, linked list, array, or other suitable data type depending on the data samples for eye movement dynamics needed to be stored in the data model.

In some embodiments, the control unit 414 may include a data model generator 422. The data model generator 422 is a module that receives eye movement data collected by the sensing arrangement 412 during a modeling step as described below. The data model generator 422 may extract, or cause the data analysis module 416 to extract, information from the collected eye movement data that will constitute the threshold eye movement data samples in the data model. The data model generator 422 may then create the data model from the threshold eye movement data samples, and may store the data model in the data model store 420. In other embodiments, the data model may be generated and stored in the data model store 420 by a separate modeling unit (not shown) of the system 400. The modeling unit may include its own sensing arrangement, processing hardware, and program modules. One suitable modeling unit is described with respect to the above study (i.e., using the EyeLink 1000).

The control unit 414 may include or communicate with an alerting arrangement 424 configured to produce an alert to the user according to the results of the data comparison in the comparison module 418. The alerting arrangement 424 may be any suitable indicator and associated hardware and software for driving the indicator. Suitable indicators include, without limitation: a visual display such as one or more light-emitting diodes, a liquid crystal display, a projector, and the like; a bell, buzzer, or other audible signaling means; and a piezoelectric or other vibrating device. In an embodiment, the alerting arrangement 424 may receive an alert signal generated by, for example, the comparison module 418 when a threshold deviation in the eye movement dynamics is detected.

Figure 5:
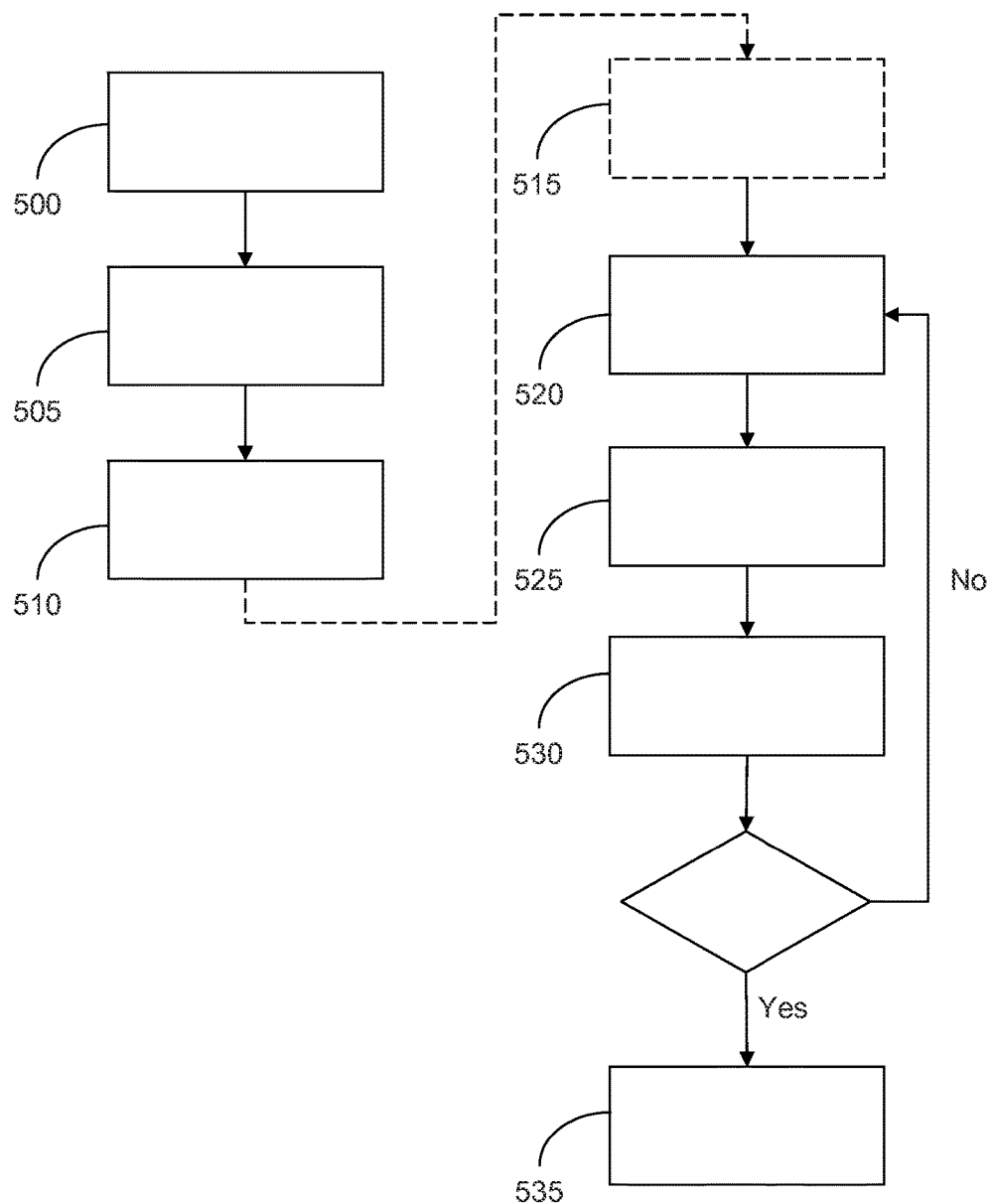
FIG. 5 is a flowchart illustrating a method for detecting hypoxia in accordance with the present invention.

The detection system 400 may be used to execute any suitable method of detecting dangerous conditions that are indicated by eye movement data. Referring to FIG. 5, the detection system 400 may execute a method of detecting onset or presence of hypoxia in the user. At step 500, the system may record baseline measurements of the eye movement dynamics for the data model. The baseline measurements are taken of a subject which may or may not be the user. It may be advantageous that the data model use baseline measurements of the user himself in order to individualize the operation of the system, but the baseline measurements may be taken from a non-user subject, or taken from a plurality of subjects and averaged if desired. The conditions in which the baseline measurements are recorded may depend on the desired specificity of the data model. In some embodiments, the baseline measurements may be taken in normal (i.e., sea-level or other typical atmospheric oxygen supply) conditions. In other embodiments, the baseline measurements may be taken in oxygen-depleted or known hypoxic conditions. In still other embodiments, as in the study described above, the baseline measurements may be taken continuously or at predetermined intervals as the subject is exposed to a progression from normal to hypoxic conditions.

At step 505, the system 400 may calculate one or more threshold drift velocities from the recorded baseline measurements. The threshold drift velocities may depend on the format of the collected baseline measurements. For example, where only normal-condition or only hypoxic-condition baseline measurements were taken, a single threshold drift velocity (i.e., threshold-normal or threshold-hypoxic drift velocity) may be calculated. Where progressive baseline measurements were obtained, one or more threshold drift velocities reflecting the subject's progression into, and degree of, hypoxia may be calculated. At step 510, the system 400 may generate the data model for the baseline-tested subject(s). The data model may represent the progression of the intersaccadic drift velocity of the subject from normal conditions to hypoxic conditions, and further beyond a hypoxic threshold into increasingly severe hypoxia. The data model may be generated and stored in any suitable format that allows the system 400 to subsequently compare eye movement data collected in situ from the user against the data model to determine the user's current susceptibility to hypoxia.

The steps 500, 505, 510 for obtaining the data model may be performed at any suitable time before testing the user in situ for signs of hypoxia. In one embodiment, the steps 500-510 may be performed far in advance and remotely from the test environment. In another embodiment, the steps 500-510 may be performed in the test environment, immediately preceding testing the user. For example, the user may activate the system 400, such as by donning and activating eyewear housing the sensing assembly 12, which initiates step 500 of recording the baseline measurements in the present conditions. Typically, this would be in normal conditions, such as when the user is a scuba diver about to dive off of his boat or a pilot preparing to fly an aircraft, and only the normal or non-hypoxic eye movement data would be collected as baseline measurements. In still other embodiments, the data model may be created by the system 400 or another system using a different method than described above.

At step 515, optionally the system 400 may calibrate itself to the user if the data model or comparison method require it. For example, the data model may be a standardized model generated from baseline measurements of (a) non-user subject(s), or the comparison method may determine the presence of hypoxia from a percentage deviation from the user's threshold-normal drift velocity value(s). See below. In such an embodiment, the system 400 calibrates (step 515) by recording a calibration set, such as ten seconds or less but preferably five seconds or less, of eye movement data of the user when the system 400 is activated in the test environment under normal conditions. The system 400 may compare the calibration data to the data model. In one embodiment, this involves determining a deviation of the user's threshold-normal drift velocity from the threshold-normal drift velocity of the model. The system 400 can then adapt the data model to the user.

At step 520, the system 400 may record in situ eye movement data from the user continuously or at predetermined intervals while the system 400 is activated. At step 525, the system 400 may calculate, in real-time or at predetermined intervals, the user's current drift velocity. At step 530, the system 400 may compare the current drift velocity to the data model to determine the user's progression (or lack thereof) toward hypoxia. Such progression may be calculated within any suitable paradigm. Examples include, without limitation: ratio or percentage by which the current drift velocity exceeds the user's or the data model's threshold-normal drift velocity; ratio or percentage by which the current drift velocity is below or above the threshold-hypoxic drift velocity; comparison of current drift velocity to points on a curve between threshold-normal and threshold-hypoxic values in the data model; and the like. If the user is neither hypoxic nor within a predetermined proximity to the threshold-hypoxic value of the data model, the system 400 returns to step 520 and continues recording current data. If the user's condition warrants (i.e., the current drift velocity is above or within a certain range of the threshold-hypoxic value), at step 535 the system 400 may alert the user to take corrective action.

The described systems and methods may be implemented in any environment and during any task that may subject the user to dangerous conditions that affect eye movements. The various configurations presented above are merely examples and are in no way meant to limit the scope of this disclosure. Variations of the configurations described herein will be apparent to persons of ordinary skill in the art, such variations being within the intended scope of the present application. In particular, features from one or more of the above-described configurations may be selected to create alternative configurations comprised of a sub-combination of features that may not be explicitly described above. In addition, features from one or more of the above-described configurations may be selected and combined to create alternative configurations comprised of a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

What is claimed is:

1. A system, comprising:
a sensing arrangement including a camera that collects eye movement data of a user;
an alerting arrangement that produces one of a visual, an audio, and a vibrational alert to the user in response to receipt of an alert signal; and
a control unit in communication with the sensing arrangement and the alerting arrangement, the control unit comprising processing hardware configured to analyze the eye movement data and generate the alert signal, including:
a data analysis module configured to extract one or more current eye movement dynamics from the eye movement data; and
a comparison module configured to receive the one or more current eye movement dynamics from the data analysis module and compare the one or more current eye movement dynamics to one or more baseline eye movement dynamics accessible by the control unit, and to send the alert signal to the alerting arrangement in response to a determination that one or more of the compared current eye movement dynamics diverges from one or more of the baseline eye movement dynamics by a threshold amount indicating one of onset and presence of hypoxia in the user.

2. The system of claim 1:
wherein the current eye movement dynamics include one or more intersaccadic drift velocities of the user and the data analysis module is configured to calculate the one or more intersaccadic drift velocities; and
wherein the comparison module is configured to compare one or more of the intersaccadic drift velocities to one or more threshold drift velocities of the baseline eye movement dynamics.

3. The system of claim 2, wherein one of the intersaccadic drift velocities comprises a drift mean velocity, and wherein when the drift mean velocity is different from the one or more threshold drift velocities by more than the threshold amount, the alert signal comprises an alert of the presence of hypoxia in the user.

4. The system of claim 2, wherein one of the intersaccadic drift velocities comprises a current intersaccadic drift velocity, and wherein when the current intersaccadic drift velocity is different from the one or more threshold drift velocities by more than the threshold amount, the alert signal comprises an alert of the onset of hypoxia in the user.

5. The system of claim 4, wherein the current intersaccadic drift velocity is collected by the sensing arrangement within ten seconds of the comparison module sending the alert signal to the alerting arrangement.

6. The system of claim 4, wherein the data analysis module calculates the current intersaccadic drift velocity by:
identifying, in the eye movement data, a drift period comprising a duration and a distance; and
determining the intersaccadic drift velocity from the duration and the distance.

7. The system of claim 1, wherein the eye movement dynamics include one or more saccade parameters.

8. The system of claim 7, wherein the saccade parameters comprise a saccadic peak velocity and a magnitude, and wherein the comparison module is configured to compare the current saccadic peak velocity and magnitude to one or more threshold saccadic peak velocities and magnitudes of the baseline eye movement dynamics.

9. The system of claim 1, wherein the eye movement data is collected from both eyes of the user.

10. The system of claim 1, wherein the baseline eye movement dynamics are obtained from a data model stored in a model data store accessible by the control unit.

11. The system of claim 10, wherein the data model is a standardized model generated from baseline measurements of one or more non-user subjects.

12. The system of claim 11, wherein the control unit is configured to calibrate the data model to the user by:
obtaining, from the sensing arrangement when the user is in a non-hypoxic state, a calibration set of eye movement data;
comparing the calibration set to the standardized model to determine a deviation of the calibration set from the standardized model; and
adapting the data model to the user based on the deviation.

13. The system of claim 12, wherein the calibration set comprises a threshold-normal drift velocity for the user, and wherein comparing the calibration set to the standardized model comprises comparing the threshold-normal drift velocity for the user to a threshold-normal drift velocity for the standardized model.

14. The system of claim 10, wherein the control unit further comprises a data model generator configured to generate the data model by:

obtaining, from the sensing arrangement when the user is in a non-hypoxic state, a portion of the eye movement data;
extracting from the portion of the eye movement data a plurality of threshold eye movement data samples; and
creating the data model from the threshold eye movement data samples.

15. A method of determining a physiological state of a user, the method comprising:
recording from the user, during a time-on-duty of the user, eye movement data of one or both of the user's eyes without interrupting an activity of the user using a camera;
comparing the eye movement data to one or more baseline measurements using a control unit in communication with the camera and including processing hardware configured to analyze the eye movement data and generate an alert; and
if the eye movement data diverges from one or more of the baseline measurements by a threshold amount, indicating one of onset and presence of hypoxia in the user, delivering the alert to the user via an alerting arrangement in communication with the control unit.

16. The method of claim 15, wherein the eye movement data comprises one or both of saccade parameters and intersaccadic drift parameters.

17. The method of claim 16, further comprising calculating a current intersaccadic drift velocity of the user from the eye movement data, wherein comparing the eye movement data to the baseline measurements comprises comparing the current intersaccadic drift velocity to a threshold intersaccadic drift velocity of the baseline measurements.

18. The method of claim 17, wherein the alert indicates to the user that a hypoxic condition of the user exists.

19. The method of claim 15, further comprising recording the baseline measurements from the user in non-hypoxic conditions.

20. The method of claim 15, further comprising:
obtaining a standardized data model of eye movement dynamics;
recording one or more threshold eye movement data samples from the user in non-hypoxic conditions;
determining a deviation of the threshold eye movement data samples from one or more eye movement dynamics of the standardized model; and
using the deviation to calibrate the standardized data model to include the baseline dynamics.

* * * * *